(12) United States Patent
Alizadeh et al.

(10) Patent No.: US 8,230,703 B2
(45) Date of Patent: Jul. 31, 2012

(54) METHOD FOR MAKING SPME FIBERS

(76) Inventors: Reza Alizadeh, Tehran (IR); Sharmin kharrazi, Tehran (IR); Nahid Mashkouri Najafi, Tehran (IR)

( * ) Notice: Subject to any disclaimer, the term of this patent is extended or adjusted under 35 U.S.C. 154(b) by 367 days.

(21) Appl. No.: 12/508,578

(22) Filed: Jul. 24, 2009

(65) Prior Publication Data

US 2010/0000261 A1 Jan. 7, 2010

(51) Int. Cl.
*C03B 37/016* (2006.01)
(52) U.S. Cl. .......... 65/440; 427/108; 427/110; 427/169
(58) Field of Classification Search .................... 65/440; 427/108, 110, 169
See application file for complete search history.

(56) References Cited

U.S. PATENT DOCUMENTS

| | | | |
|---|---|---|---|
| 6,759,126 B1 * | 7/2004 | Malik et al. | 428/391 |
| 2002/0034827 A1 * | 3/2002 | Singh et al. | 436/177 |
| 2005/0142039 A1 * | 6/2005 | Chen et al. | 422/101 |

* cited by examiner

*Primary Examiner* — Queenie Dehghan
(74) *Attorney, Agent, or Firm* — Barry Choobin; Choobin & Choobin Consultancy LLC

(57) ABSTRACT

It is disclosed a method for making SPME fibers. The SPME fibers consist of metal-oxide coatings on fused-silica fibers. The coatings are prepared from a water-based solution containing a predetermined amount of metal ion and a predetermined amount of a reactant. The water based solution and the fused-silica fibers are kept at the temperatures below 100° C. for a predetermined time to obtain SPME fibers. The SPME fibers are applied for extraction of pesticides and other organic compounds such as 1,4-dichloro-2-nitrobenzene; Biphenyl; and Acenaphthene in the water based solution and cooling gas of a power generator respectively.

7 Claims, No Drawings

METHOD FOR MAKING SPME FIBERS

SPONSORSHIP STATEMENT

The present invention for international filing is sponsored by The Iranian Nanotechnology initiative Council.

FIELD OF INVENTION

The present invention relates to a stationary phase for Solid Phase Micro Extraction (SPME).

BACKGROUND OF THE INVENTION

Solid-phase micro extraction (SPME) is based on the partition/adsorption of analytes to a stationary phase coated on a fused-silica fiber. SPME is an attractive alternative to traditional sample treatment and preparation methods, because it combines sample extraction, pre-concentration following by sample introduction, altogether into one step and can be readily combined with gas chromatography (GC) or high performance liquid chromatography (HPLC). This method has gained increasing application in many areas including environmental, food and drug analysis.

Almost all commercially available SPME fibers are based on fused-silica fiber. The coating techniques include pasting with adhesives, electrochemical polymerization or deposition, direct-pasting, chemical corrosion, and the sol-gel technique.

In general, organic polymers are the most widely used coatings for the extraction of organic compounds. However, some inorganic coatings based on graphite materials and metallic compounds have also exhibited good performance in SPME.

Adsorption of compounds depends on the functional groups on the stationary phase and surface area. Increasing the surface area increases the sensitivity of analysis and lowers the limit of detection. In this way, metal oxides such as $Al_2O_3$, $ZnO$, $ZrO_2$, and nanostructure $PbO_2$ prepared by electro-oxidizing or electro-deposition techniques have been used as SPME coatings. Metal oxide-based SPME coatings made of a mixture of $Al_2O_3$ on a polyvinylchloride matrix dispersed in tetrahydrofuran and $Nb_2O_5$ coating using a metallo-organic decomposition technique have also been successfully used.

By applying an inexpensive and effective aqueous growth technique at mild temperatures functionalized coating of metal oxide materials on fused silica is achieved. Such a technique allows the generation of advanced nano/micro particulate coatings without using any template, membrane, surfactant, applied external fields, or specific requirements in fused silica activation, thermal stability, or crystallinity. Such a process avoids the safety hazards of organic solvents and their eventual evaporation and potential toxicity. In addition, because no organic solvents or surfactants are present, the purity of the materials is substantially improved. The residual salts are easily washed out by water due to their high solubility. In most cases, no additional heat or chemical treatments are necessary, which represents a significant improvement compared with surfactant, template, membrane base, corrosion or electrochemical synthesis methods.

The present invention method is applicable to all water-soluble metal ions likely to precipitate in solution.

Therefore, it would be advantageous to provide a method to overcome the above shortcomings.

SUMMARY OF THE INVENTION

The primary object of the present invention is to provide a method for making SPME fibers.

Yet another object of the present invention is to provide a method in which by developing 1-D nano structures such as nano-rods and nano-wires of metal oxides, a higher surface area can be achieved.

Yet another object of the present invention is to provide a method for making nanostructure $SnO_2$ and $ZnO$ nano-rods grown on fused silica, as a new fiber for solid phase micro extraction (SPME).

Yet another object of the present invention is to provide a method for preparation of nano stationary phase of SPME with high surface area and high adsorption power of compounds such as pesticides and drugs.

Yet another object of the present invention is to provide a method for preparation of nano stationary phase of SPME by developing nano structures of metal oxide like nano-rods.

Yet another object of the present invention is to provide a method for making SPME in which a high pre-concentration and proper clean-up of samples are achieved.

Yet another object of the present invention is to provide a method for making SPME in which by applying an inexpensive and effective aqueous growth technique at mild temperatures functionalized coating of metal oxide materials on fused silica is achieved.

Yet another object of the present invention is to provide a method which allows the generation of advanced nano/micro particulate coatings without using any template, membrane, surfactant, applied external fields, or specific requirements in fused silica activation, thermal stability, or crystallinity.

Yet another object of the present invention is to provide a method which avoids the safety hazards of organic solvents and their eventual evaporation and potential toxicity.

Yet another object of the present invention is to provide a method to improve the purity of the materials. The residual salts are easily washed out by water due to their high solubility. In most cases, no additional heat or chemical treatments are necessary, which represents a significant improvement compared with surfactant, template, membrane base, corrosion or electrochemical synthesis methods.

Yet another object of the present invention is to provide a method to improve repeatability and stability of stationary phase.

Yet another object of the present invention is to provide a stationary phase which consists of metal-oxide (bulk as well as nanostructured) coated fiber for the adsorption of volatile and semi-volatile compounds.

Yet another object of the present invention is to provide a method for making SPME fibers which extracts the compounds at trace levels.

DETAILED DESCRIPTION OF THE INVENTION

Example 1

Materials and Apparatus 1,4-dichloro-2-nitrobenzene (DCNB), Biphenyl (BPh), Acenaphthene (ANPh), Tin (IV) chloride pentahydrate and Urea were purchased from Fluka. Zinc nitrate tetrahydrate and Hexamethylenetetramine (HMT) were purchased from Fluka. The SPME Syringe was purchased from Azar Electrode Company (Tabriz, Iran). Fused Silica optical fibers were purchased from Polymicro Technologies Inc (Phoenix, Ariz.). Hydrochloric acid, Methanol and acetone were purchased from Merck. GC-MS separations were carried out by an Agilent Technologies 6890N Network GC System and Agilent Technologies 5973 Network Mass spectrometer. The pyrolyzer was made at the Niro Research Institute (NRI). The insulators were supplied from shahid rajaee Power house (Qazvin, Iran).

Preparation of $SnO_2$ SPME Fibers

1) The fused silica fibers were cut into 35 mm lengths and the 15 mm of polymeric cover were removed by immersing to the acetone for 10 min. They were thoroughly rinsed by sonification in diluted hydrochloric acid, acetone and water respectively.

2) The Nanostructured $SnO_2$ solution was prepared according to Vayssiers method. Briefly, A typical synthesis involved the preparation of a 100 mL aqueous solution (MILLI-Q (Milli-Q®), 18.2 MWcm) consisting of 0.034 g of $SnCl_4.5H_2O$ and 0.920 g of $(NH_2)_2CO$ in presence of 5 ml of fuming HCl (37%) in a closed pyrex bottle with autoclavable screw cap.

3) The prepared fibers were hanged into the mentioned solution for 48 h at the 95° C.

4) After two days, nanostructured $SnO_2$ SPMEs (NSS-SPME) were washed by MILLI-Q (Milli-Q®), water at the Ultrasonic cleaner. Conditioning of NSS-SPMEs was performed at the injector of GCMS with 290° C. temperature for 30 min.

Extraction Conditions of DCNB, BPh and ANPh

Extraction of DCNB, BPh and ANPh were performed via Head Space extraction method simultaneously. In this method, percentage of salt (NaCl), extraction temperature, adsorption time and desorption time were optimized. After optimization, 30% (W/V) NaCl were added into a 4 ml of sea water as sample. 10 ml vial containing a magnetic stirrer bar was used in this aim. After addition of an appropriate volume of stock solution, the vial was sealed with a silicon-rubber septum and an alumina cap. The fiber was exposed to the head space of solution by piercing the septum with the SPME needle assembly and then depressing the plunger. The vial was put into the oil bath with 60° C. temperature for 30 min. After extraction, the fiber was withdrawn into the needle and removed from sample vial. The analytes were then thermally desorbed in the GC injector at 250° C. for 20 min. The Caspian Sea water was selected as real sample.

Results

A nanostructure $SnO_2$ solid phase micro extraction (NSS-SPME) fiber was performed to extract some pesticides such as DCNB, BPh and ANPh from seawater.

For the linear study eight concentration solution including: 0.001, 0.01, 10, 1000, 10000, $1\times10^5$, $1\times10^6$, $1\times10^7$, $5\times10^7$ $ngl^{-1}$, were evaluated and four of them were in the linear range. The linear dynamic ranges (LDR) are $0.1$-$100\,\mu gl^{-1}$ for measurement of all pesticides. The linear regression values, limit of detections (LOD) and relative standard deviations (RSD, n=5) for DCNB, BPh and ANPh were evaluated (Table 1). Also, the RSD values for the separation and measurement of analytes (repeatability for one fiber and fiber-to-fiber RSD) were shown in Table 1 which are quite acceptable. The limits of detection of all pesticides are too low (at the $ngl^{-1}$ level). It is due to high surface area for adsorption of pesticides.

TABLE 1

Analytical performance of the method for the analysis of DCNB, BPh and ANPh by NSS-SPME.

| Analyte | LDR ($\mu gl^{-1}$) | $R^2$ | RSD % (n = 5) One fiber | Fiber-to-Fiber | LOD ($ngl^{-1}$) | Caspian Sea water Found | Recovery (%)** |
|---|---|---|---|---|---|---|---|
| 1,4-dichloro-2-nitrobenzene | 0.1-100 | 0.999 | 9.8 | 12.5 | 10 | n.d.* | 93 |
| Biphenyl | 0.1-100 | 0.998 | 7.7 | 7.8 | 0.1 | n.d. | 97 |
| Acenaphthene | 0.1-100 | 0.999 | 4.9 | 8.9 | 0.001 | n.d. | 98 |

*Not detected
**Recoveries were determined by spiking of 10 $\mu gl^{-1}$ of standard solutions.

Example 2

Monitoring of Insulator Degradation Products of Generator via NSS-SPME

Generators are most important at the electrical distribution system. Temperature affect on the production power and life time of generator. Cooling fluid is used for decreasing of insulator temperature at the generator. Air and hydrogen are common cooling fluid. Because of some electrical errors, the insulators are pyrolized and produce volatile organic compounds. Accurate determination of these compounds can help to distinguish the life time of generator. In this aim, we tried to develop an off line method to denote volatile organic compounds resulted from pyrolysis of insulator.

Sampling Method 1) 0.5 gr of insulator was put inside the pyrolyzer and the NSS-SPME was set at the end of the pyrolyzer.

2) After 10 min that pyrolyzer reached to 700° C., Helium as carrier gas carried out all of the volatile organic compounds on the NSS-SPME fiber for 5 min.

3) After that, The NSS-SPME was taken from pyrolyzer and injected to the GC-MS via SPME syringe.

Results

There are some volatile organic compounds resulted from pyrolysis of insulator, adsorption of these compounds on the NSS-SPME is related to compound and fiber structures. Analysis by GC-MS showed that the NSS-SPME is capable to adsorb all of the polar and nonpolar compounds. Table 2 shows the list of most compound which resulted from insulator pyrolysis.

TABLE 2

The list of compounds adsorbed by NSS-SPME

Compounds name

1. Cyclotrisiloxane, hexamethyl
2. 2-Propenoic acid, 2-methyl-, butyl ester
3. Phenol
4. Cyclotetrasiloxane, octamethyl
5. Phenol, 2-methyl-
6. Hexanoic acid, 2-ethyl-
7. Cyclopentasiloxane, decamethyl-
8. Ethanol, 2-phenoxy-
9. Phenol, 2-ethyl-
10. O-DIMETHYLAMINOBENZALDEHYDE
11. Benzene, 2,4-diisocyanato-1-methyl
12. Tetrasiloxane, decamethyl-
13. Cyclohexene, 4-methyl-
14. 4-Methoxy-3-(3-methoxyphenyl)-4-methylpentan-1-ol
15. Dibutyl phthalate
16. N-ethyl-1,3-dithioisoindoline
17. Cyclohexasiloxane, dodecamethyl-
18. Benzene, 1,2,4,5-tetramethyl- Example 3

Preparation of Nanorod ZnO-SPME Fibers

1) The fused silica fibers were prepared according to instruction described in example 1.
2) The nanorod ZnO solution was prepared according to Vayssiers method. Briefly, a typical synthesis involved the preparation of 100 mL aqueous solution (MILLI-Q (Milli-Q®), 18.2 MWcm) 0.005 M of Zn $(NO_3)_2 \cdot 4H_2O$ and HMT in a closed pyrex bottle with autoclavable screw cap.
3) The prepared fibers were hanged into the mentioned solution for several hours at the 95° C.
4) The Nanorod ZnO SPMEs (NRZ-SPME) were washed by MILLI-Q (Milli-Q®), water at the Ultrasonic cleaner. Conditionings of NRZ-SPMEs were performed at the injector of GC-MS with 290° C. temperature for 30 min.

Extraction Conditions of DCNB, BPh and ANPh

Extraction of DCNB, BPh and ANPh were performed via Head Space extraction method simultaneously according to the process described in Example 1.

Results

Some nanostructure metal oxides such as nanobelts, nanoribbons, nanodisks, nanosheets, and nanodendrites have low area to extract materials such as pesticides, insecticides and drugs. Development of nanostructure materials to 1-D and 3-D nanomaterials such as nanorods, and nanotubes lead to high surface area to determine trace analysis. In addition to the economical manufacturing of nanomaterials, a better fundamental knowledge of their electronic structure, physical, interfacial, and structural properties, as well as their stability is required to fully exploit their fascinating physical and chemical potential.

A nanorod ZnO solid phase microextraction (NRZ-SPME) fiber was performed to extract mentioned pesticides from sea water.

For the linear study eight concentration solution including: 0.001, 0.01, 10, $1\times10^5$, $1\times10^6$, $1\times10^7$, $5\times10^7$ $ngl^{-1}$, were evaluated. The linear dynamic range (LDR) is 100-10000 $\mu gl^{-1}$ for DCNB while it is too broader for BPh and ANPh (0.1-10000 $\mu gl^{-1}$) than DCNB. LDR for analysis of all pesticides by NRZ-SPME are broader when compare to those of NSS-SPME. The linear regression values, limit of detections (LOD) and relative standard deviations (RSD, n=5) for DCNB, BPh and ANPh were evaluated (Table 3). Also, the RSD values for the separation and measurement of analytes (repeatability for one fiber and fiber-to-fiber RSD) were shown in Table 3. The limit of detection of measurement of BPh by NRZ-SPME is lower than that of NSS-SPME, while the limits of detection of measurement of the other pesticides are the same for both of the fibers. The RSD of measurements by NRZ-SPME for one fiber and fiber-to-fiber analysis in the same sample are much lower than those of NSS-SPME in the same condition.

TABLE 3

Analytical performance of the method for the analysis of DCNB, BPh and ANPh by NRZ-SPME.

| Analyte | LDR ($\mu gl^{-1}$) | $R^2$ | RSD % (n = 5) | | LOD ($ngl^{-1}$) | Caspian Sea water | |
| --- | --- | --- | --- | --- | --- | --- | --- |
| | | | One fiber | Fiber-to-Fiber | | Found | Recovery (%)** |
| 1,4-dichloro-2-nitrobenzene | 1-10000 | 0.995 | 6.5 | 11.4 | 10 | n.d.* | 91 |
| Biphenyl | 0.1-10000 | 0.999 | 4.3 | 7.6 | 0.001 | n.d. | 102 |
| Acenaphthene | 0.1-10000 | 0.999 | 4.9 | 7.3 | 0.001 | n.d. | 98 |

*Not detected
**Recoveries were determined by spiking of 10 $\mu gl^{-1}$ of standard solutions.

Example 4

Monitoring the Insulator Degradation Products of Generator by NRZ-SPME

Sampling Method

The sampling process is completely like to example 2. Briefly, 0.5 gr of insulator was sat at the pyrolyzer and the NRZ-SPME was stood at the end of the pyrolyzer. After 10 min that pyrolyzer reached to 700° C., Helium as carrier gas carried out all of the volatile organic compounds on the NRZ-SPME fiber for 5 min. After that, The NRZ-SPME was taken from pyrolyzer and injected to the GC-MS via SPME syringe.

Results

There are only ten volatile organic compounds resulted from pyrolysis of insulator that can be adsorbed by both NRZ-SPME and NSS-SPME. However, both of these fibers are made up of metal oxide, therefore, the capability of adsorption of compounds by these two fibers are different and are due to the type-nanostructure. Adsorption of these compounds on these two fibers depend on compound and fiber structures. Analysis by GC-MS showed that both these SPME fibers are capable to adsorb all of the polar and nonpolar compounds. Table 4 shows the compounds resulted from pyrolysis of insulator and adsorbed by NRZ-SPME.

TABLE 4

The list of compounds adsorbed by NRZ-SPME

| | Compounds name |
|---|---|
| 1 | 2-Propanone |
| 2 | Cyclotrisiloxane, hexamethyl- |
| 3 | Phenol, 4-methyl- |
| 4 | 2-Propenoic acid, 2-methyl-, 2-methylpropyl ester |
| 5 | Phenol |
| 6 | Cyclotetrasiloxane, octamethyl- |
| 7 | Phenol, 2-methyl- |
| 8 | Phenol, 3-ethyl- |
| 9 | Tetrasiloxane, decamethyl- |
| 10 | Cyclopentasiloxane, decamethyl- |
| 11 | Ethanol, 2-phenoxy- |
| 12 | 2,4-DI-(P-HYDROXYPHENYL)-4-METHYLPENT-1-ENE |
| 13 | Cyclohexasiloxane, dodecamethyl- |
| 14 | Cyclohexene, 4-methyl- |
| 15 | cis-2-ethyl-3-methyl-6-[(E)-4-methylpent-2-en-2-yl]-5,6-dihydro-2H-pyran |
| 16 | 6-methylthio[1]benzothieno[2,3-c]quinoline |
| 17 | 21-(trimethylsilyloxy)medroxyprogesterone-3-methoxime |
| 18 | 2-Propenoic acid, 2-methyl-, butyl ester |

The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of the invention which is limited only by the following claims.

We claim:

1. A method for making solid phase micro extraction (SPME) fibers, wherein said method consists of steps:

Obtaining a predetermined amount of fused silica fibers covered by polymeric cover, wherein said fused silica fibers are cut into 35 mm lengths; removing 15 mm of polymeric cover from said 35 mm length and obtaining a predetermined amount of naked fused silica fibers;

Rinsing sequentially said predetermined amount of naked fused silica fibers by sonification in diluted hydrochloric acid, acetone and water respectively; preparing a solution consisting of 100 mL aqueous solution wherein said aqueous solution consists of a predetermined amount of metal ions soluble in water, a predetermined amount of oxidant with a predetermined pH;

Inserting said predetermined amount of naked fused silica fibers into said solution for a predetermined time at a predetermined temperature, and obtaining a plurality of nanostructured $SnO_2$ attached to said naked fused silica fiber and obtaining a SPME fibers.

2. The method as claimed in claim 1, wherein said method further comprises step of washing said SPME fibers with Milli-Q® water by an Ultrasonic cleaner.

3. The method as claimed in claim 1 wherein said method further comprises step of conditioning said SPME fibers at 290° C. temperature for 30 min.

4. The method as claimed in claim 1, wherein said predetermined amount of metal ions soluble in water is 0.034 g of $SnCl_4.5H_2O$.

5. The method as claimed in claim 1, wherein said predetermined amount of oxidant is 0.920 g of $(NH_2)_2CO$.

6. The method as claimed in claim 1, wherein said predetermined amount of pH is set by 5 mL of fuming HCl (37%).

7. The method as claimed in claim 1, wherein said predetermined temperature is below 100° C. for preparation of said SPME fibers.

* * * * *